United States Patent [19]

Burr et al.

[11] 4,064,498

[45] Dec. 20, 1977

[54] ELECTRICAL CIRCUITRY FOR DETECTING A COMBUSTIBLE MIXTURE OF GAS IN A MINE ATMOSPHERE

[75] Inventors: John F. Burr, Pittsburgh; Homayoun Hadi, Library, both of Pa.

[73] Assignee: Consolidation Coal Company, Pittsburgh, Pa.

[21] Appl. No.: 750,877

[22] Filed: Dec. 15, 1976

Related U.S. Application Data

[63] Continuation-in-part of Ser. No. 625,848, Oct. 28, 1975, abandoned.

[51] Int. Cl.² ............................................. G08B 21/00
[52] U.S. Cl. ............................... 340/237 R; 23/255 E
[58] Field of Search .................. 340/237 R; 73/27 R; 23/232 E, 254 E, 255 E; 324/71 R, 71 SN

[56] References Cited

U.S. PATENT DOCUMENTS

| | | | |
|---|---|---|---|
| 3,147,465 | 9/1964 | Brown et al. | 340/237 R |
| 3,311,455 | 3/1967 | Robinson | 340/237 R X |
| 3,399,398 | 8/1968 | Becker et al. | 340/237 R |
| 3,482,233 | 12/1969 | Ogg | 340/237 R |
| 3,496,558 | 2/1970 | Willson et al. | 340/237 R |
| 3,519,391 | 7/1970 | Winter et al. | 340/237 R X |
| 3,678,489 | 7/1972 | Scherban et al. | 340/237 R |
| 3,717,858 | 2/1973 | Hadden | 340/237 R X |
| 3,815,114 | 6/1974 | Johnson et al. | 340/237 R |
| 3,879,717 | 4/1975 | Gruensfelder | 340/237 R |
| 3,887,335 | 6/1975 | Boutonnat | 23/254 E |

*Primary Examiner*—John W. Caldwell, Sr.
*Assistant Examiner*—Daniel Myer
*Attorney, Agent, or Firm*—William A. Mikesell, Jr.; Stanley J. Price, Jr.; John M. Adams

[57] ABSTRACT

A pair of sensor assemblies that change in electrical resistance when exposed to a mixture of combustible gas are positioned at a selected location in a mine or on a piece of operating equipment and receive power for continuous operation from a regulated power source. Regulator devices maintain a preselected input signal to the sensor assemblies. When exposed to a mixture of combustible gas, the sensor assemblies generate output signals which are received by a comparator and switch assembly. If an output signal of a sensor assembly exceeds a preselected signal of the comparator associated therewith, an alarm signal is generated and an audible and visual alarm device is actuated to indicate the presence of a combustible mixture of gas in the mine atmosphere. A time delay mechanism is operable to interrupt the input signal to the sensor assemblies if the alarm signal continues longer than a preselected interval. The time delay mechanism also generates a latch signal to continue generation of the alarm signal when the presence of combustible gas has been detected. The regulator device for each sensor assembly transmits an amplified signal proportional to the sensor output signal to a signal deviation detector. If the difference between the amplified signals of the sensor assemblies exceed a preselected value, the signal deviation detector also transmits an output signal to the above alarm device and time delay mechanism.

15 Claims, 9 Drawing Figures

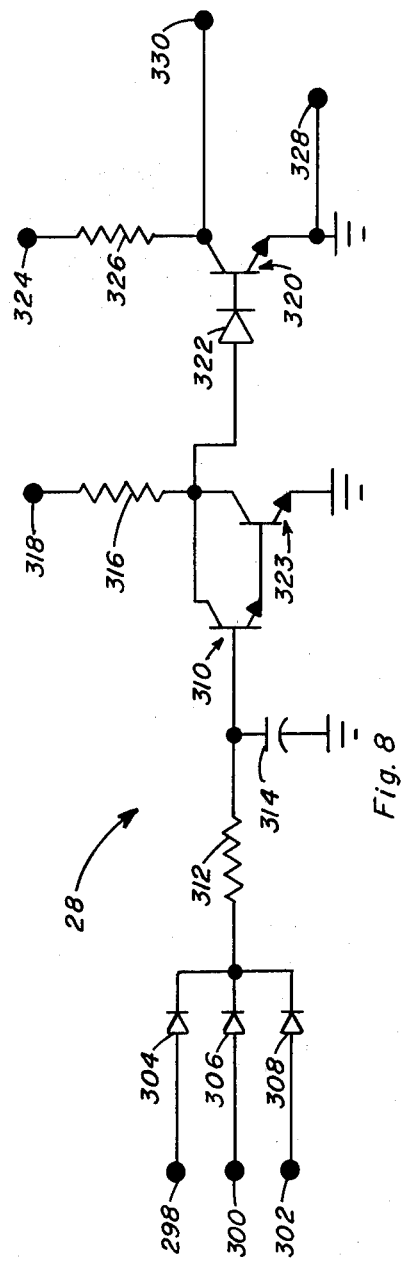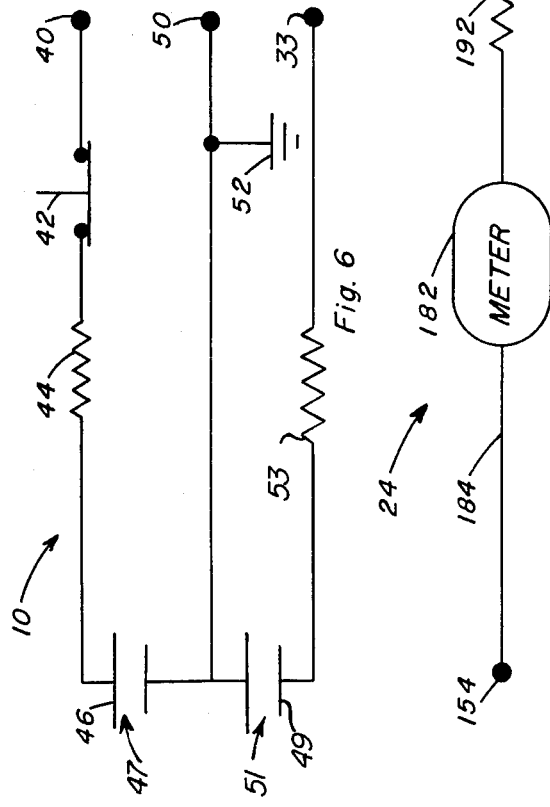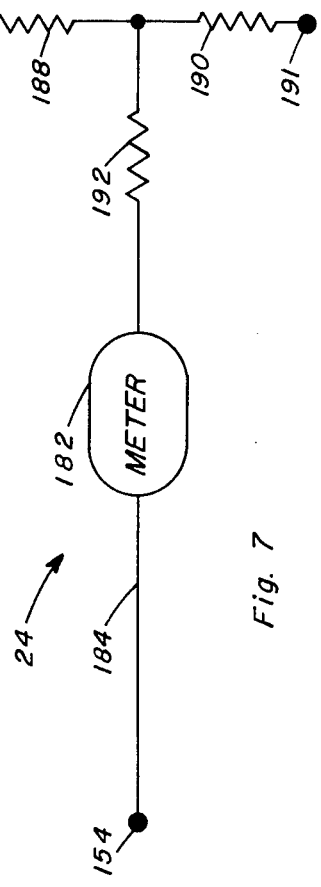

ELECTRICAL CIRCUITRY FOR DETECTING A COMBUSTIBLE MIXTURE OF GAS IN A MINE ATMOSPHERE

CROSS-REFERENCE TO RELATED APPLICATION

This application is a continuation-in-part of application, Ser. No. 625,848, filed on Oct. 28, 1975, and now abandoned, entitled "Electrical Circuitry For Detecting A Combustible Mixture Of Gas In A Mine Atmosphere".

BACKGROUND OF THE INVENTION

1. Field of the Invention

This invention relates to electrical circuitry for detecting a combustible mixture of gas in a mine atmosphere and more particularly to an electrical combustible gas detector that includes a pair of sensor assemblies that operate continuously for a preselected time interval to generate output signals that are compared to a preselected signal and actuate an alarm system when a combustible mixture of gas is detected in the mine atmosphere.

2. Description of the Prior Art

In underground mining operations solid material is dislodged from the mine face by the operation of cutting machines and as a consequence methane gas is emitted from the rock strata. The gases may accumulate in pockets in the mine presenting a threat of explosion in the presence of a spark. Only by monitoring the concentration of the mixture of gases in the mine atmosphere is it possible to determine whether the mixture of gases has reached a critical concentration.

One method of monitoring the mixture of combustible gases in the mine atmosphere involves the use of a conventional flame safety lamp. The accuracy of a flame safety lamp, however, is dependent on the skill of the operator and only the most skilled operator can detect combustible mixtures in a concentration of less than 1% with a flame safety lamp. Even though such a concentration may not be deemed critical, detecting a combustible mixture at this level of concentration is essential in order to determine the source of the gas emission for possible accumulation to a critical level. Another disadvantage of the flame safety lamp as an indicator of combustible gas in the mine atmosphere is the difficulty in using the device within one foot of the mine face where the concentration of gases is generally the greatest and the threat of explosion the most severe. In fact, in many cases the operator is exposed to a greater hazard, such as from a roof fall, if he is required to sample the concentration of methane gas within one foot of the mine face.

Electronic devices for monitoring combustible gases are known in the art and include a single sensing head that transmits a signal through a change in electrical resistance that is proportional to the gas/air ratio. The signals are amplified and transmitted to indicator and alarm circuits which when actuated alert the operator to hazardous gas concentrations. Such devices, however, have not proved to be acceptably accurate, particularly in a mine atmosphere.

There is need for apparatus for continuously monitoring the atmosphere of a mine for the presence of a combustible mixture of gases that are emitted from the face during the mining operation. The apparatus must be capable of accuracy to below 1% concentration in air for extended intervals. The apparatus must also be adaptable for positioning at selected points in the mine, particularly at the mine face and on operating equipment.

SUMMARY OF THE INVENTION

In accordance with the present invention there is provided electrical circuitry for detecting a combustible mixture of gas in a mine atmosphere that includes sensor assemblies for continuously monitoring the level of combustible gas in the mine atmosphere. The sensor assemblies are operable to supply output signals that are proportional to the concentration of the combustible mixture of gas in the mine atmosphere. A power source actuates the sensor assemblies. Regulator devices maintain a preselected input signal to the sensor assemblies and include detectors for comparing the output signals of the sensor assemblies with a preselected signal and generate an input signal proportional to the output signals of the sensor assemblies. A comparator device is connected to the regulator devices and the power source. The comparator is operable to receive input signals proportional to the output signals from the sensor assemblies from the regulator devices and to generate a corresponding output signal that is proportional to the maximum input signal received. An alarm device is provided for actuating a preselected alarm to indicate the presence of a combustible mixture of gas in the mine atmosphere. The alarm device is arranged to receive an output signal from the detector of the current regulator for actuating the alarm signal when the output signal from either sensor assembly exceeds a preselected value indicating the presence of a combustible mixture of gas in the mine atmosphere. A meter device is connected to the power source and the comparator device and is operable to record the maximum value of the input signals received by the comparator from the regulators. A signal deviation mechanism receives input signals from the regulator devices and is operable to actuate the alarm device and thereby indicate an excess deviation between the output signals of the sensor assemblies.

A time delay mechanism receives amplified output signals from the regulator detector and the signal deviation mechanism. If the condition of the presence of combustible gas in the mine atmosphere or of an excess deviation between the output signals of the sensor assemblies occurs, the time delay mechanism is actuated to terminate the preselected input signal to the sensor assembly and thereby deenergize the sensors after a preselected time interval. In addition, the timer generates a latch signal which is transmitted to the alarm device to indicate the undesirable condition.

Accordingly, the principle object of the present invention is to provide electrical circuitry for detecting a combustible mixture of gas in a mine atmosphere that operates continuously at selected locations in the mine for a selected time interval to generate output signals that are proportional to concentration of combustible gas in the mine atmosphere and actuate an alarm device when an undesirable condition occurs.

Another object of the present invention is to provide an electrical combustible gas detector for operation in a mine that includes a pair of temperature sensitive sensor assemblies that are responsive to the presence of a combustible mixture of gas in the mine atmosphere and generate output signals for actuating alarm devices that are latched by a time delay mechanism to continue the alarm.

A further object of the present invention is to provide an electrical combustible gas detector that includes a signal deviation device that continuously monitors the output signals of the sensor assemblies and terminates operation of the sensor assemblies and actuates the alarm device if the difference between the value of the output signals exceeds a preselected value.

An additional object of the present invention is to provide an electrical system for detecting the presence of combustible gas in a mine atmosphere that is efficiently located for operation at desired positions in the mine and is capable of detecting a 1.0% mixture of combustible gas in the mine atmosphere.

Another object of the present invention is to provide an electrical combustible gas detector for use in a mine that provides a continuous readout of the concentration of combustible gas in the mine atmosphere.

These and other objects and advantages of this invention will be more completely disclosed and described in the following specification, the accompanying diagrams, and the appended claims.

BRIEF DESCRIPTION OF THE DRAWINGS

FIG. 6 is an electrical schematic, illustrating the apparatus for supplying power to the sensor assemblies.

FIG. 7 is a schematic diagram, illustrating the circuitry for selectively recording the output signals generated by the sensor assembly.

FIG. 8 is an electrical schematic, illustrating the time delay mechanism for terminating power to the sensor assemblies and actuating an alarm signal when a combustible mixture of gas has been detected in the mine atmosphere and when an excess deviation between the output signals of the sensor assembly has been recorded.

DESCRIPTION OF THE PREFERRED EMBODIMENTS

Figure 1:
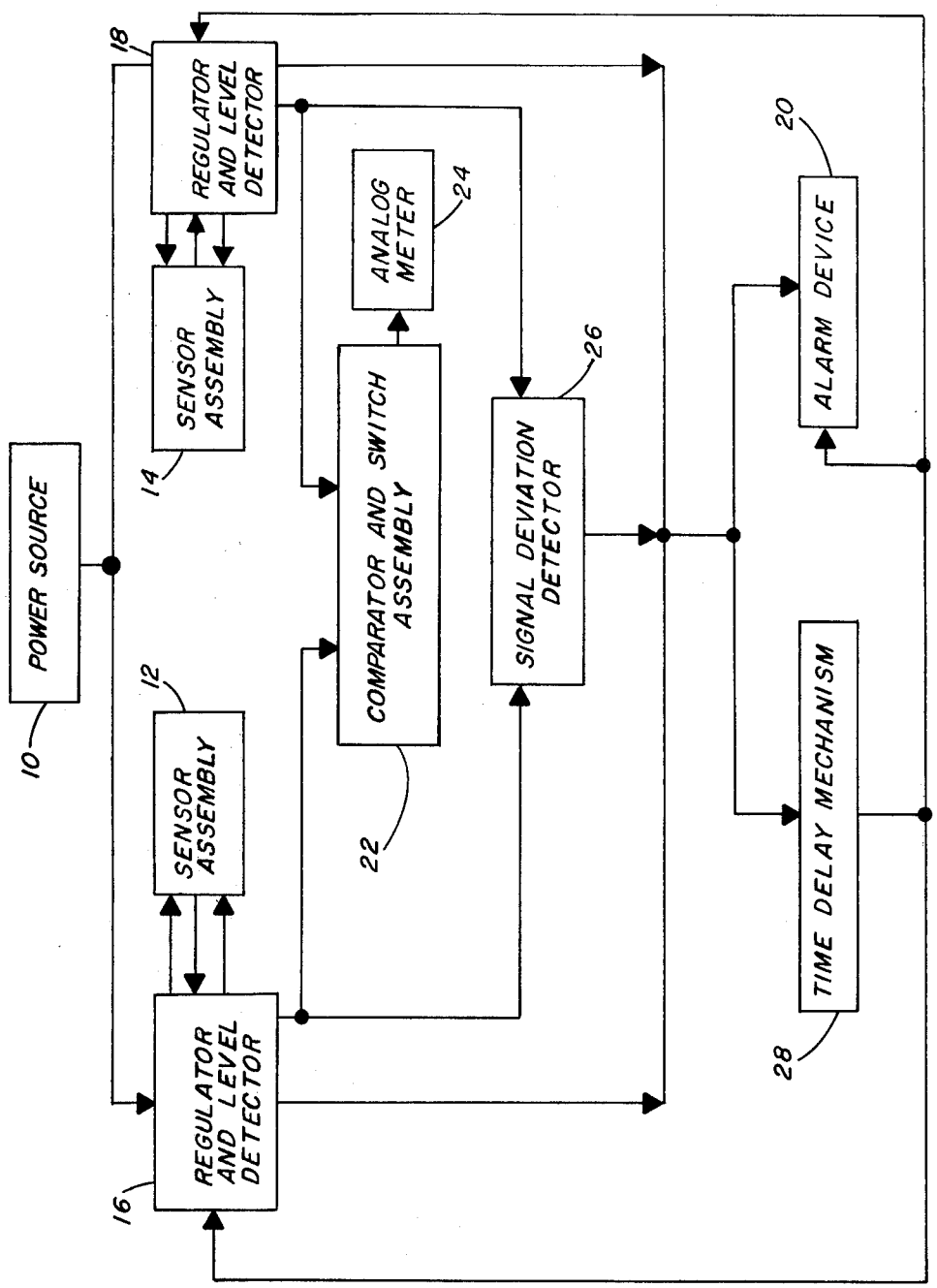
FIG. 1 is a block diagram, illustrating the elements of the electrical circuitry for detecting a combustible mixture of gas in a mine atmosphere.

Referring to the diagrams and particularly to FIG. 1 there is illustrated a block diagram of the elements provided in the electrical circuitry for detecting a combustible mixture of gas in a mine atmosphere that includes a source of power, such as a battery pack 10, that supplies power to a pair of independent sensor elements 12 and 14 that are connected to the battery pack 10 through regulators 16 and 18 respectively. The regulators 16 and 18 maintain a preselected input signal to the sensor assemblies 12 and 14 regardless of any variation that may occur in the power supply voltage or a change in the resistance of the sensor assemblies. The sensor assemblies 12 and 14 may be suitably mounted at selected points in the mine or on the machinery operating in the mine to continuously monitor the mine atmosphere for the presence of a combustible mixture of gas, specifically methane gas.

The sensor assemblies 12 and 14 generate output signals that are received by the regulators 16 and 18 and the magnitude of the signals are compared by a level detector of the regulators with a preselected signal. In the event the output signals generated by the sensor assemblies 12 and 14 exceed a preselected signal supplied by the regulators 16 and 18, the regulators generate a responsive signal that is transmitted to an alarm device 20 that is actuated to thereby indicate the presence of a combustible mixture of gas in the mine atmosphere. The alarm device may comprise both audible and visual alarm signals.

The regulators 16 and 18 supply input signals to a comparator and switch assembly 22 in which the input signal received is proportional to the output signals generated by the sensor assemblies 12 and 14. The input signals from the regulators 16 and 18 are compared by the comparator 22 and the greater of the input signals is selected for readout by a meter 24 that receives current from the comparator and switch assembly 22. In this manner a continuous readout of the maximum output signal generated by sensor assemblies 12 and 14 is provided. In addition, the operation of the switch of the comparator 22 momentarily interrupts the output to the meter 24 to provide a reading of the lower value of the output signals received by the comparator 22 from the sensor assemblies 12 and 14.

The output of the regulators 16 and 18, responsive to the output signals generated by the sensor assemblies 12 and 14, is also transmitted to a signal deviation detector 26. The signal deviation detector 26 compares the magnitude of the input signals from the regulators 16 and 18 which input signals are proportional to the respective signals received from the sensor assemblies 12 and 14. If an excess deviation of preferably greater than 7.5% is recorded between the inputs from the regulators 16 and 18, the detector 26 generates an output signal that is transmitted to the alarm device 20. In this manner the operator is alerted to a possible malfunction of the sensor assemblies as indicated by the undesirable deviation between the output signals of the sensor assemblies recorded by the regulators 16 and 18.

In the event a combustible mixture of gas is detected by the sensor assemblies 12 and 14 a corresponding output signal is transmitted to the detector of the current regulators 16 and 18. The regulators will transmit a corresponding output signal to a time delay mechanism 28. After having received the output signal from either one of the regulators 16 and 18, indicating a dangerous condition as a result of combustible mixture in the mine atmosphere, the timer 28 will generate a responsive output signal back to the regulators 16 and 18. This terminates current flow through the monitoring circuits of the regulators to cease operation of the sensor assemblies 12 and 14.

In an alarm condition the timer 28 is also operable to actuate the alarm device to generate a continuous signal indicating the presence of a combustible mixture of gas in the mine atmosphere. Furthermore, the timer 28 is operable to receive output from the signal deviation detector 26 when an excess deviation is recorded between the output signals of the sensor assemblies 12 and 14. In a similar manner the timer 28 will terminate operation of the sensor assemblies 12 and 14 by transmitting an input signal to regulators 16 and 18 and also actuate the alarm device 20.

Figure 2:
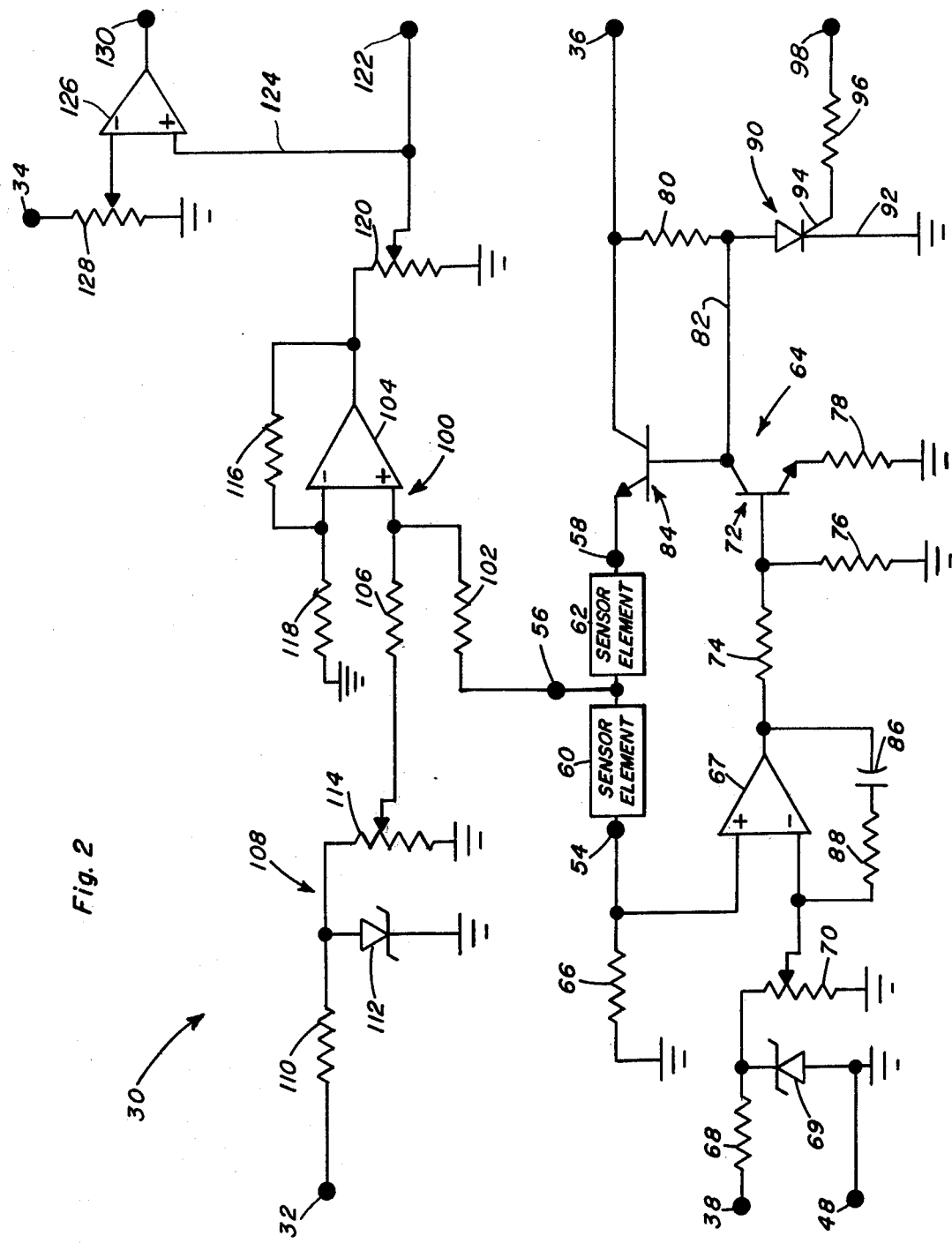
FIG. 2 is an electrical schematic, illustrating a current regulator for the sensor elements and the current level detector circuit for indicating the presence of a combustible mixture of gas in the mine atmosphere.

Referring to the FIG. 2 there is illustrated circuitry 30 for each of the regulators 16 and 18 of FIG. 1 that includes terminal 32, which is connected to terminal 33 of battery pack 10, illustrated in FIG. 6, and also includes terminals 34, 36 and 38 that are connected to terminal 40 of battery pack 10, illustrated in FIG. 6. Referring to FIG. 6, the terminal 40 is connected by switch 42 and resistor 44 to the positive terminal 46 of battery 47 to supply positive voltage to the terminal 40. Terminal 48 of circuitry 30 in FIG. 2 is connected by terminal 50 to the electrical ground 52 of the battery pack 10. Terminal 33 is connected through resistor 53 to the negative terminal 49 of battery 51 so that negative voltage is supplied to terminal 33 and hence to terminal 32 of FIG. 2.

Each of the regulators 16 and 18 is connected by terminals 54, 56 and 58 to one of the respective sensor assemblies. Each of the sensor assemblies as illustrated in FIG. 2 includes an active element 60 and an inactive element 62. The electrical resistance of the active sensor element 60 is temperature sensitive and will therefore change when exposed to a mixture of combustible gas. The inactive sensor element 62 is similar to the active element 60 but is not temperature sensitive when exposed to the gas but may compensate for ambient changes in temperature, humidity, and atmospheric pressure in the mine.

In the embodiment of circuitry 30 illustrated in FIG. 2, regulators 16 and 18 of FIG. 1 function as current regulators. With this arrangement the current regulator circuit 30 includes a monitoring circuit 64 for continuously supplying a preselected current to the elements 60 and 62 of the sensor assembly for each of the current regulators 16 and 18. In this manner a constant current flow is maintained through the respective sensor elements regardless of a variation in the power supply voltage from the power pack 10 or variations in the resistance of the sensor elements. A resistor 66 is connected to ground and the terminal 54 of the sensor element 60. The voltage appearing across resistor 66 by the flow of current from the sensor assembly is compared by an operational amplifier 67 to a preselected reference voltage. The reference voltage received by the amplifier 67 is controlled by a Zener diode 69 connected by a resistor 68 and terminal 38 to the positive voltage of the battery pack 10. The voltage supply is adjustable by potentiometer 70. With this arrangement an increase in current flow through the sensor elements 60 and 62 will accordingly increase the voltage across resistor 66 and the voltage input to the operational amplifier 67 to thus switch the output of the amplifier to a more positive state.

Figure 2A:
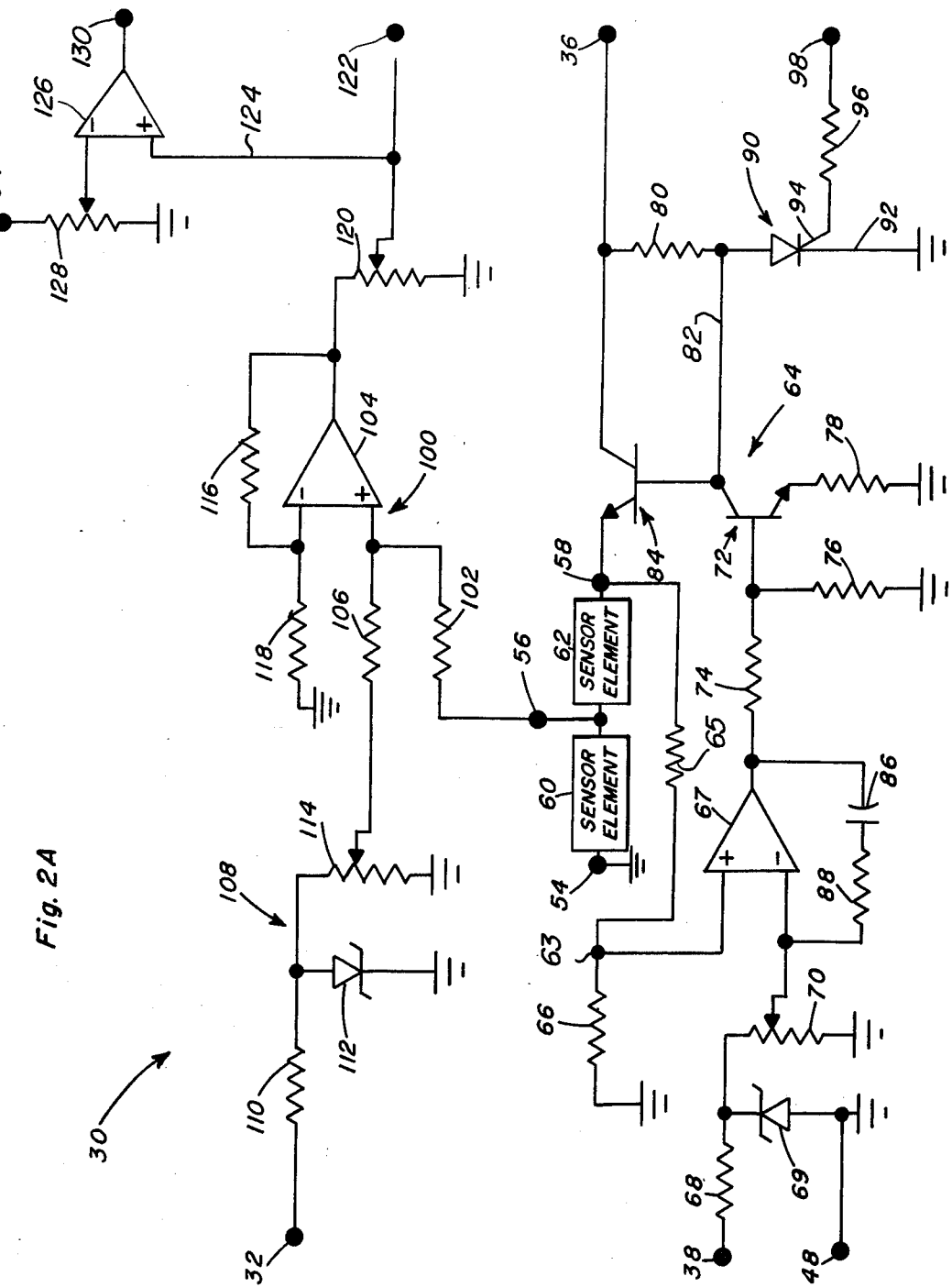
FIG. 2A is an electrical schematic similar to FIG. 2, illustrating a voltage regulator for the sensor elements in place of a current regulator.

Further in accordance with the present invention regulators 16 and 18 are operable to function as voltage regulators as illustrated in FIG. 2A. In this manner a constant voltage is maintained across the respective sensor elements regardless of a variation in the power supply voltage from the power pack 10 or variations in the resistance of the sensor elements. Sensor element 60 is connected by terminal 54 to ground. The resistors 65 and 66 are connected to ground and the terminal 58 of the sensor element 62. The voltage appearing between resistors 65 and 66 at terminal 63 is compared by an operational amplifier 67 to a preselected reference voltage. The reference voltage received by the amplifer 67 is controlled by a Zener diode 69 connected by a resistor 68 and terminal 38 to the positive voltage of the battery pack 10. The voltage supply is adjustable by potentiometer 70. With this arrangement an increase in the voltage across the sensor elements 60 and 62 will accordingly increase the voltage at terminal 63 and the voltage input to the operational amplifier to a more positive state.

A transistor 72 is connected by a voltage divider comprising resistors 74 and 76 to the operational amplifier 67. Switching the output of the amplifier 67 to a more positive state as a consequence of an increase in the input signal to the sensor elements correspondingly increases the base current of the transistor 72 through the voltage dividers 74 and 76 and resistor 78 connecting the emitter of transistor 72 to ground. An increase in base current of the transistor 72 also increases the collector current supplied through resistor 80 and conductor 82. Thus, the base voltage of the transistor 72 is reduced to, in turn, reduce current to a regulator transistor 84 having an emitter connected to terminal 58 of the sensor element 62. A reduction in the current to the regulator transistor 84 reduces the input signal to the sensor elements 60 and 62 to the preselected level.

In the event the input signal to the sensor elements 60 and 62 should fall below the preselected level, the voltage across resistor 66 and applied to the operational amplifier 67 will accordingly decrease thus switching the operational amplifier 67 to a more negative state. This has the effect of decreasing the base current of the transistor 72. A decrease in the transistor base current also decreases the collector current supplied through resistor 80 and conductor 82. Thus, the base voltage and current to the regulator transistor 84 is increased to increase the input signal to the sensor element 60 and 62 to the preselected value.

A capacitor 86 and resistor 88 form a feedback loop for the operational amplifier 67 so that the output thereof is an amplified sum of the input signal regulated by the Zener diode 69 and resistor 68 and an integral thereof. In this manner undesirable oscillations in the output of the operational amplifier 67 are prevented to improve the performance thereof.

A silicon controlled rectifier 90 is included in the monitoring circuit 30 and has an anode connected to conductor 82 and a cathode connected to ground conductor 92. Gate terminal 94 of rectifier 90 is connected by a limiting resistor 96 to terminal 98. Terminal 98 is connected to the time delay mechanism 28 and the alarm device 20. The silicon controlled rectifier 90 is normally retained in a nonconductive state in the absence of current flowing from the terminal 98 through the resistor 96 to the gate terminal 94. The applicaton, however, of a high voltage signal at the gate terminal 94 from terminal 98 actuates rectifier 90 to become conductive between the anode and cathode and thereby direct current flow from transistor 72 through conductor 82 to the ground conductor 92. Thus, regulator transistor 84 is maintained in a nonconducting state by interrupting base current flow through transistor 84 by actuation of the silicon controlled rectifier 90. In this manner the rectifier 90 is utilized to latch the regulator transistor 84 in a nonconducting state to terminate current flow through the sensor assemblies 12 and 14 under conditions where there exists a prolonged combustible mixture of gas in the mine atmosphere or an excess deviation between the magnitude of the output signals of each of the sensor assemblies 12 and 14.

The sensor elements 60 and 62 of each of the sensor assemblies 12 and 14, illustrated in FIG. 1, generate an output signal that varies with a change in resistance of the respective sensor elements as a consequence of the concentration of combustible gases in the mine atmosphere. The output signals are transmitted through terminal 56 to the level detector circuit 100 of the regulator and level detector. The sensor output signal is transmitted through a resistor 102 to operational amplifier 104. The operational amplifier 104 is connected by resistor 106 to a voltage regulating apparatus 108 that includes a resistor 110 and Zener diode 112 connected to terminal 32 of the power pack 10. In this manner a preselected voltage level regulated by potentiometer 114 is applied to the operational amplifier 104 to generate an equal but opposite current flow to that of the sensor assembly output signal through resistor 102. In this manner a zero net voltage appears at the input of the operational amplifier 104. With the above described arrangement the output of the operational amplifier 104 may be adjusted to a preselected value. A portion of the amplifier output is fed back to the input through resistor 116 and is combined with input through resistor 118 to preset the gain of operational amplifier 104. The output of the operational amplifier 104 is transmitted to a potentiometer 120 so that the output voltage may be adjusted for readout and comparison purposes.

The adjusted output voltage of the operational amplifier 104 is transmitted to terminal 122 that is connected to the comparator and switch assembly 22 and the signal deviation detector 26. The adjusted output signal is also transmitted from the potentiometer 120 through conductor 124 to comparator 126. The comparator 126 compares the adjusted output of the operational amplifier 104, which is responsive to the output signals generated by the sensor elements 60 and 62, with the input received from terminal 34 connected to the power pack 10 through potentiometer 128. If the adjusted voltage from amplifier 104 is greater than the preset input from terminal 34, the comparator 126 switches to a positive state to generate an output signal of a positive voltage that is transmitted through terminal 130 to activate the alarm device 20 and the time delay mechanism 28. The presence of a positive output voltage at the terminal 130 indicates the existence of a combustible mixture of gas in the mine atmosphere.

Figure 3:
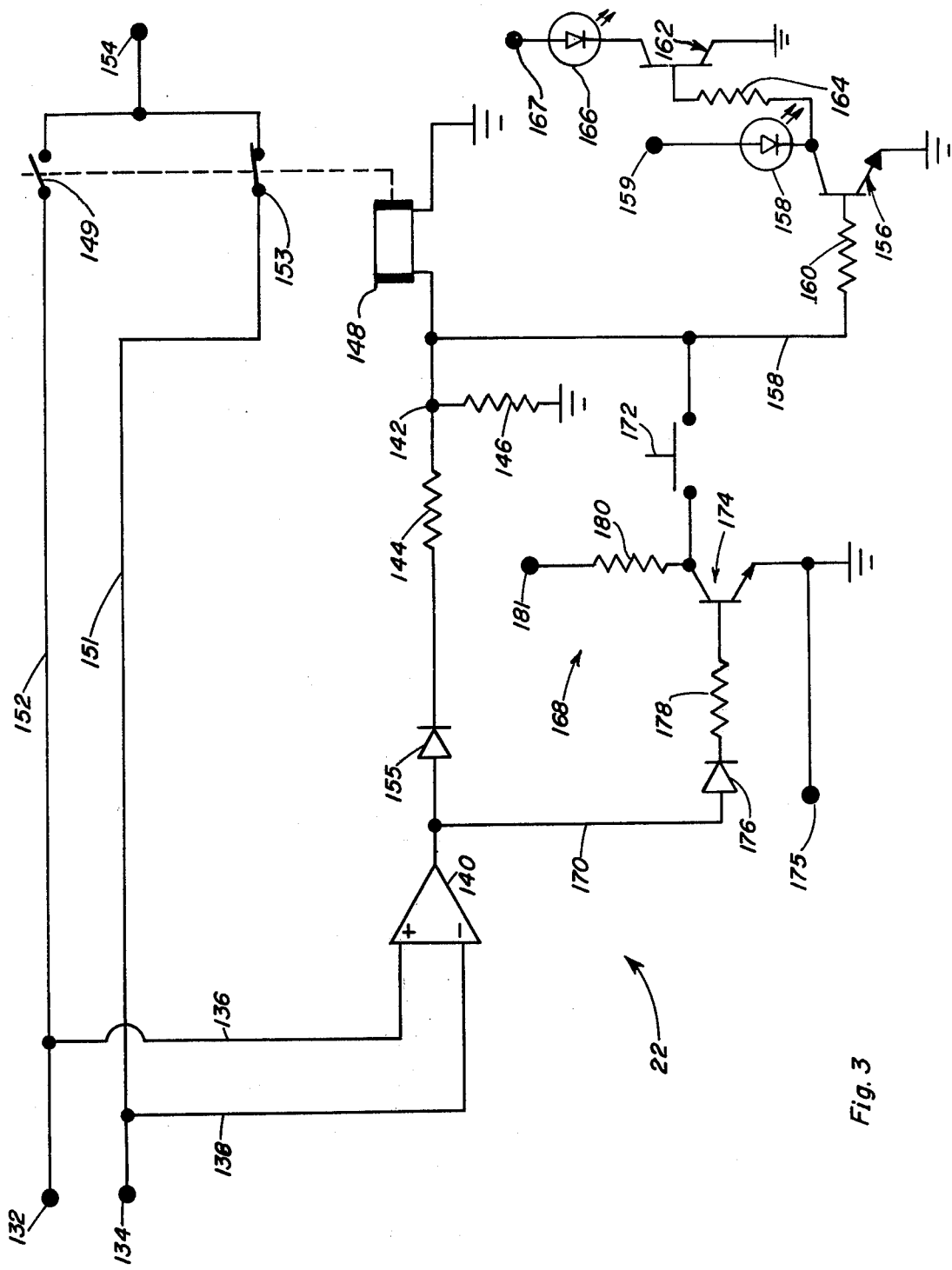
FIG. 3 is an electrical schematic, illustrating the comparator and switch apparatus for monitoring the output signals generated by the sensor assemblies and for indicating the maximum sensor output signal received.

The adjusted output signals transmitted from the operational amplifier 104 of each of the regulators 16 and 18 is transmitted to terminals 132 and 134 of the comparator and switch assembly 22 illustrated in FIG. 3. The comparator and switch assembly 22 is operable to compare the magnitude of the adjusted output signals received from the regulators and indicate quantitatively the greater value of the output signals received from the sensor assemblies 12 and 14 and also provide an indication as to which sensor assembly generates the greater output signal.

The regulator 16 supplies an amplified signal which is proportional to the output signal generated by the sensor assembly 12 to the terminal 132. Accordingly, regulator 18 supplies an amplified signal which is proportional to the output signal generated by the sensor assembly 14 to the terminal 134. The respective signals from terminals 132 and 134 are transmitted by conductors 136 and 138 as input to an operational amplifier 140. The resultant output of the operational amplifier 140 is positive when the amplified signal from terminal 132 is greater than the amplified signal from terminal 134. With the operational amplifier 140 switched to a high output state, a positive voltage appears across voltage divider 142 that includes resistor 144 and resistor 146. The positive voltage generated from the amplifier 140 actuates the relay 148 to close the normally open contacts 149 to permit current flow from terminal 132 through conductor 152 to terminal 154. Terminal 154 is connected to the analog meter 24. In this manner the meter 24 is actuated to provide a quantitative indication of the output signal generated by the sensor assembly 12 and thus an indication of the concentration of combustible gases in the mine atmosphere as recorded by sensor 12.

If the amplified signal generated by the regulator 16 in response to the output signal of sensor assembly 14 is greater than the amplified signal from terminal 132, the output of operational amplifier 140 is switched to a negative state and the current flow to the resistor 144 is blocked by diode 155. Consequently, the amplified signal from terminal 134 passes through conductor 151 and the normally closed contact 153 of relay 148 to the terminal 154. The output from terminal 154 generated by the amplified signal from terminal 134 provides a quantitative readout of the output signal generated by sensor assembly 14 in response to the concentration of combustible gases in the mine atmosphere.

When the operational amplifier 140 is switched to a high output state, base current is supplied to the transistor 156 through conductor 158 and resistor 160. Transistor 156 is actuated when the amplified signal from terminal 132 exceeds the amplfied signal from terminal 134, and current flows through the collector of transistor 156 to indicator 158 that is connected by terminal 159 to the positive voltage of the power source. The indicator 158 is actuated to thereby indicate that the sensor assembly 12 is being monitored for readout by the meter 24. With the operational amplifier 104 in a high output state, current flow to the base of transistor 162 connected by resistor 164 to transistor 156 is terminated to thereby cease operation of indicator 166. The indicator 166 is connected by terminal 167 to the positive voltage of the power source. If the amplified signal from terminal 134 exceeds the signal from terminal 132, amplifier 140 switches to a low output state and current flows through resistor 164 to the base of transistor 162 to activate transistor 162 and the indicator 166. In this manner, monitoring of sensor assembly 14 for readout by the meter 24 is indicated.

An inverter circuit 168 is connected across the operational amplifier 140 and transistor 156 and 162 by conductors 170 and switch 172 respectively. The inverter circuit 168 is operable to override the output signal of the amplifier 140 to momentarily provide an indication of the lower value of the amplified signals received from the detectors of regulators 16 and 18. An inverter transistor 144 receives the output from amplifier 140 through diode 176 and resistor 178 to provide a base current for transistor 174. The emitter of transistor 174 is connected to the negative terminal of the power source 10 through terminal 175 and to ground.

With the operational amplifier 140 in a high output state, the inverter transistor 174 is actuated resulting in current flow through resistor 180 and a low voltage condition at the collector of transistor 174. Resistor 180 is connected by terminal 181 to the positive voltage of the power source. With this arrangement the collector of transistor 174 is at a low output stage when the amplifier 140 is at a high output state. Accordingly, when the output of operational amplifier 140 is low, the collector of transistor 174 is high.

A manual switch 172 connects the conductor 158 with the collector of transistor 174. By manually actuating the switch 172 to close the circuit between the collector of transistor 174 and the relay 148, a voltage level opposite to that of the output of amplifier 140 is imposed on inputs to the relay 148 and the transistor 156. This effects a change of state of the transistor 156 and the relay 148 to thereby override the output signal transmitted by the amplifier 140 so that the lower value of the amplified signals received by the comparator 22 may be momentarily monitored by the meter 24.

The meter 24 illustrated in detail in FIG. 7 receives current from the terminal 154 of the comparator and switch assembly 22, which current is proportional to the higher value of the voltages transmitted by the regulators 14 and 16 to the terminals 132 and 134 respectively of FIG. 3. The circuitry of the meter 24 illustrated in FIG. 2 includes a conventional calibrated meter 182 connected by a conductor 184 to the terminal 154. The meter 182 connected by current received from terminal 186 of power pack 10 through the resistor divider network comprising resistors 188 and 190 and the limiting resistor 192. Resistor 190 is connected to the electrical ground of battery pack 10 by terminal 191. The resistor 192 limits the current flow to the meter 182 from the power pack 10, and the resistor network permits zero calibration of the meter 182.

Figure 4:
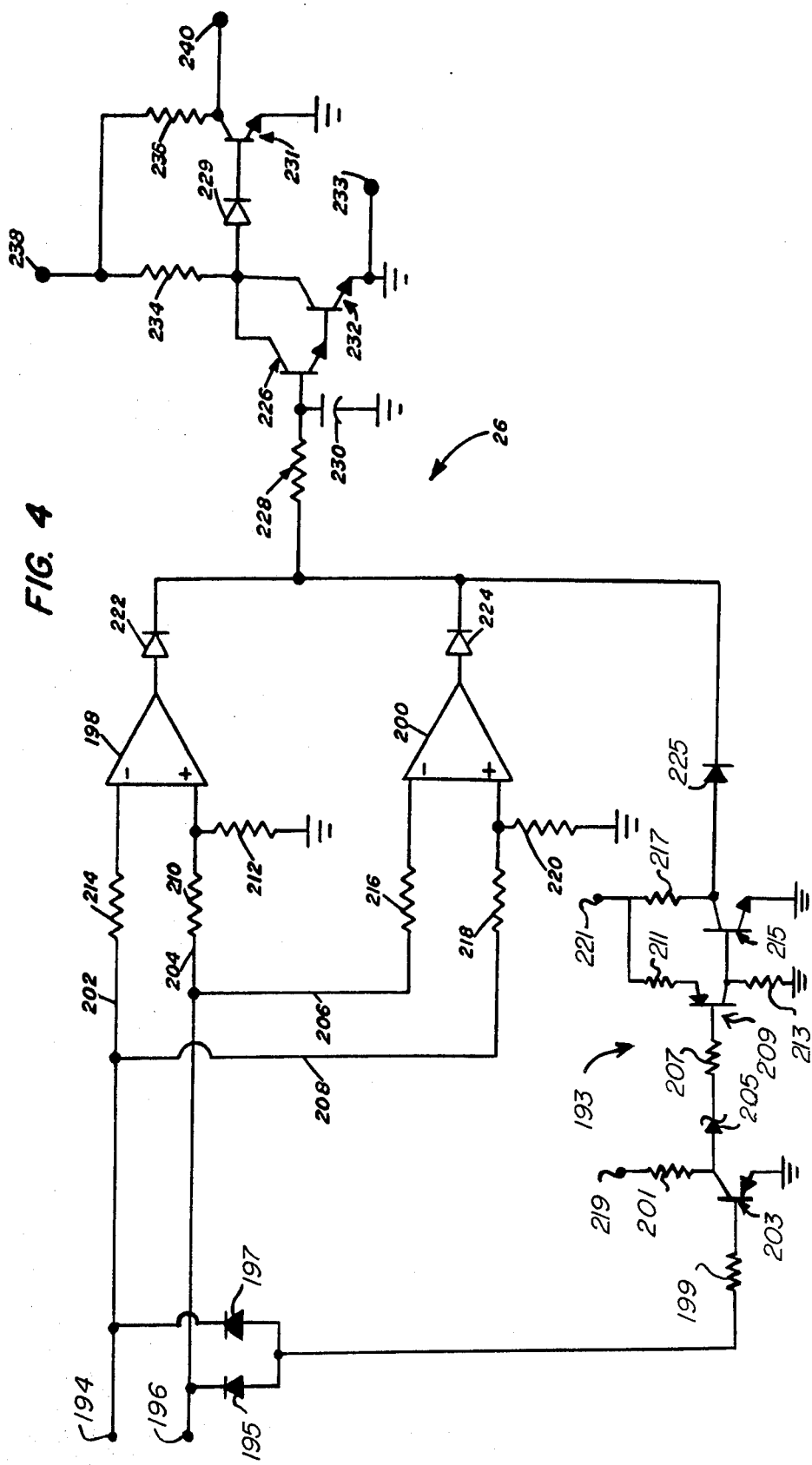
FIG. 4 is an electrical schematic, illustrating the signal deviation detector for monitoring the output signals generated by the sensor assemblies to detect an excess deviation between the sensor output signals.

Referring to FIG. 4 there is illustrated the circuitry for the signal deviation detector 26 which is operable to record an excess deviation between the output signals of the sensor assemblies 12 and 14. Amplified signals from the respective terminals of the regulators 16 and 18 are received at terminals 194 and 196. The amplified signals from the detectors are compared to each other by detector operational amplifiers 198 and 200. The amplifiers 198 and 200 are connected by conductors 202, 204, 206 and 208 to the terminals 194 and 196 respectively. A voltage divider network comprising resistors 210 and 212 connect the terminal 196 with the operational amplifier 198. With this arrangement amplified input from terminal 194 is transmitted through resistor 214 and is received by amplifier 198 which compares the input to a percentage of the input received from terminal 196 through the voltage divider network. If the amplified input from terminal 194 is lower than a percentage of the amplified input of terminal 196, the operational amplifier 198 switches to a high output state. In a similar arrangement operational amplifier 200 is connected by resistor 216 to the terminal 196 and the voltage divider network comprising resistors 218 and 220 to the terminal 194. If the amplified signal from terminal 196 is lower than the preset percentage of amplified signal from terminal 194, the amplifier 200 switches to a high output state. Therefore, as long as the voltage levels of the amplified signals from terminals 194 and 196 remain within a selected percentage of each other, the amplifiers 198 and 200 remain in a low output state.

If a deviation occurs between the respective amplified signals and the corresponding preset percentage thereof either amplifier 198 or amplifier 200 will switch to a high output state. In a high output state the switched amplifier supplies current through either of the diodes 222 or 224 to the base of transistor 226 after a preselected time delay as determined by resistor 228 and capacitor 230. The collector of transistor 226 is connected by diode 229 to transistor 231. The emitter of transistor 226 is connected to the base of a transistor 232 that is connected to the ground connection of the power source at terminal 233.

Current flow through transistor 226 supplies base current to transistor 232 to actuate transistor 232. With this arrangement current does not flow to the base of transistor 231, and consequently it remains inactive. If no excess deviation exists between the voltages of amplified signals from terminals 194 and 196, then transistors 226 and 232 remain nonconductive to thus allow the base current of transistor 231 to flow through resistor 234 and diode 228 to actuate transistor 231. Actuating transistor 231 generates current flow therethrough and resistor 236 connecting the collector of transistor 231 with terminal 238 connected to the positive voltage of power pack 10. With the transistor 231 actuated the collector thereof switches to a low level. When an excess deviation of voltage exists between the amplified signals of sensor assemblies 12 and 14, a high voltage signal is transmitted from the collector of transistor 231 to terminal 240 that is connected to the alarm device 20 and the time delay mechanism 28.

If the output signals received at terminals 194 and 196 from operational amplifier 104 (FIG. 2) of the regulator and level detectors 16 and 18 become negative because of damage to sensor elements 60 and/or 62 or because of damage to the conductors which connect regulator terminals 54, 56 and 58 to the respective sensor assemblies, diodes 196 and/or 197 conduct to supply base current to transistor 203 through base resistor 199 of a trouble circuit generally designated by the numeral 193. Current to transistor 203 actuates transistor 203 so that the collector thereof switches to ground to terminate the flow of base current to a transistor 209. For a normal condition where the trouble circuit 193 is not actuated, current flows from terminal 219 connected to the negative terminal 33 (FIG. 6) of power pack 10 through resistor 201, Zener diode 205 and resistor 207 to the base of transistor 209. Transistor 209 is actuated to direct the current through resistor 213 to ground and to the base of transistor 215 and therefrom to ground. Also, in a normal condition current from terminal 221 connected to the positive terminal 40 (FIG. 6) of power pack 10 is directed through resistor 217 to the actuated transistor 215 and to ground. The terminal 221 is connected through resistor 211 to the emitter of transistor 209.

In the event of a malfunction, as above described, current flow to transistor 209 is terminated; subsequently, transistors 209 and 215 are turned off. Current from terminal 221 is directed through resistor 217 and diode 225 to the base of transistor 226 after a preselected time delay as determined by resistor 228 and capacitor 230. As above described actuation of transistor 226 actuates the alarm device 20. In this manner a malfunction to the sensor elements is brought to the attention of the operator.

Figure 5:
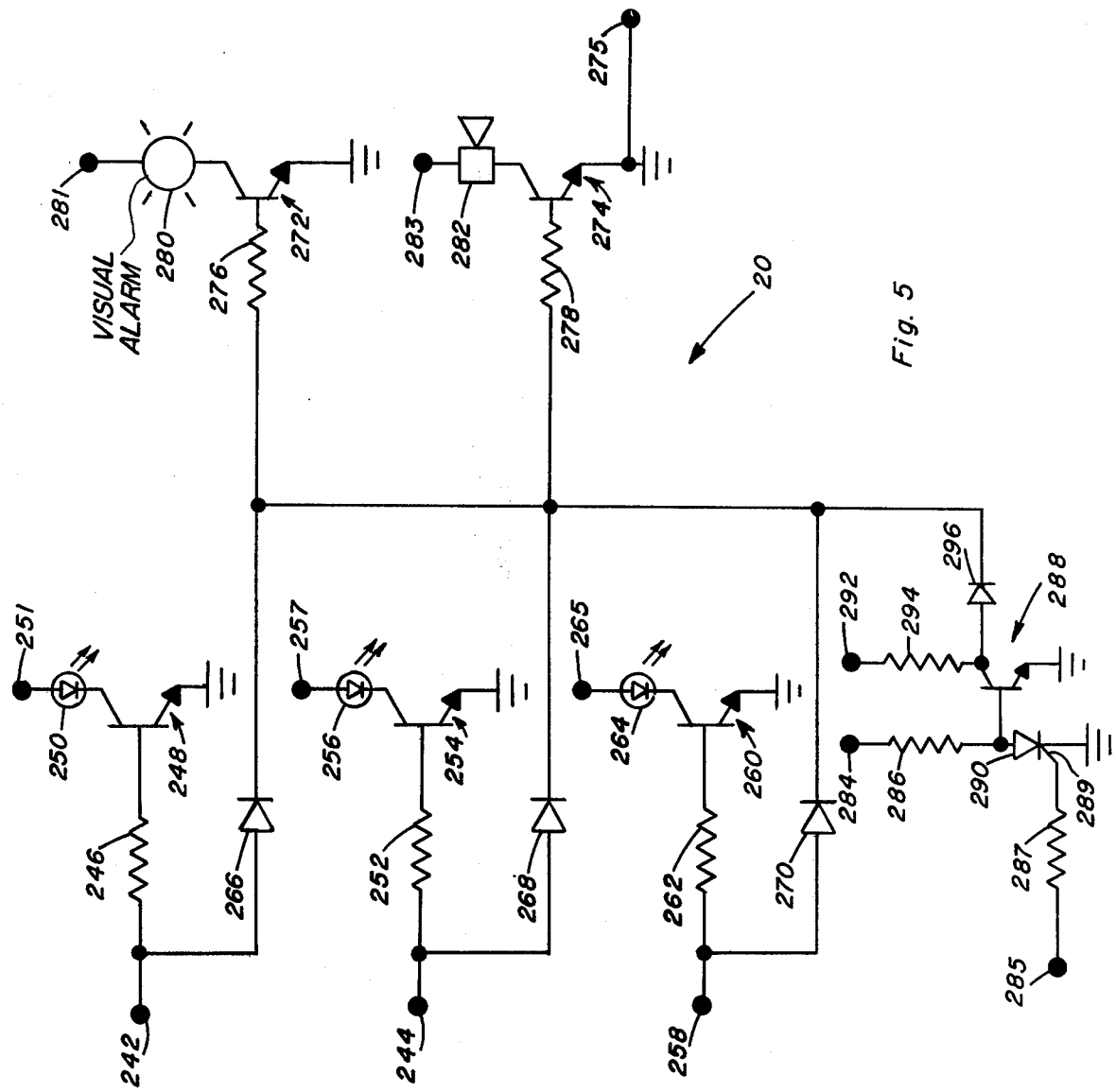
FIG. 5 is an electrical schematic, illustrating the alarm device for indicating the presence of a combustible mixture of gas in the mine atmosphere and an excess deviation between the output signals of the sensor assembly.

The alarm device 20 is illustrated in detail in FIG. 5. Each of the sensor assemblies 12 and 14 transmit output signals to the regulators 16 and 18 for conditions in which a combustible mixture of gas is detected in the mine atmosphere by the level detector circuit of each of the regulators, a high voltage alarm signal is transmitted either from sensor assembly 12 to terminal 242 or from sensor assembly 14 to terminal 244. The signals received by the alarm device 20 at terminals 242 and 244 are proportional to the amplified signals received from the respective regulators 16 and 18. A high voltage alarm signal received at terminal 242 is transmitted through resistor 246 to supply base current for transistor 248 to, in turn, actuate transistor 248 and illuminate indicator 250 that is connected by terminal 251 to the positive terminal of the power source 10. In this manner the operator is informed as to the dangerous condition presented by the mixture of combustible gas in the mine atmosphere and the source of the respective alarm signal. Similarly, the high voltage alarm signal received from the regulator 18 for sensor 14 supplies current through a resistor 252 to the base of a transistor 254. In this fashion the transistor 254 is actuated to supply current to an indicator 256, connected by terminal 257 to the positive terminal of the power source 10, and thereby actuate the indicator to indicate the presence of a combustible mixture of gas as recorded by the regulators 18 of sensor assembly 14.

When an excess deviation exists between the output signal of sensor assemblies 12 and 14, the signal deviation detector 26 is actuated to generate a high voltage level alarm signal that is transmitted to terminal 258 of the alarm device 20. The alarm signal supplies a current to the base of a transistor 260 through a resistor 262 to actuate the transistor 260 and an indicator 264 in a similar manner as above described for transistors 248 and 254. Indicator 264 is connected by terminal 265 to the positive terminal of power source 10. Each of the alarm signals received by the terminals 242, 244, and 258 are transmitted through diodes 266, 268, and 270 respectively for actuation of transistors 272 and 274. In this manner, the alarm signals provide base current for the transistors 272 and 274 through resistors 276 and 278. Thus, actuation of transistor 272, in turn, actuates visual alarm 280 and actuation of transistor 274 actuates audible alarm 282. Alarms 280 and 282 are connected by terminals 281 and 283 respectively to the positive terminal of the power source 10. The emitter of transistor 274 is connected by terminal 275 to the negative terminal of the power source 10 and to ground.

Under normal conditions base current is supplied from terminal 284 that is connected to the positive voltage of battery pack 10 to supply current through resistor 286 to transistor 288. Thus, in the absence of a high voltage level alarm signal from the regulators 16 and 18 and the signal deviation detector 26 at terminal 258, the transistor 288 remains actuated with the collector thereof maintained in a low voltage state. A silicon controlled rectifier 290 is connected by terminal 285 and limiting resistor 287 to the time delay mechanism 28 and is maintained in a normally nonconductive mode. However, the occurrence of an alarm signal to actuate the time delay mechanism 28 and generate a latch signal after a preselected time interval, applies a high voltage signal through limiting resistor 287 to the gate terminal 289 of rectifier 290. The application of a high voltage signal at the gate terminal 289 actuates the silicon vontrolled rectifier 290 to switch to a conductive state and terminate flow of the base current of transistor 288, deenergizing transistor 288. Current then flows from terminal 292 connected to the positive voltage of battery 10 through resistor 294, diode 296 and resistors 276 and 278 to actuate the visual and audible alarms 280 and 282.

As explained hereinabove a high voltage alarm signal from either of the regulators 16 or 18 indicating the existence of a combustible mixture of gas in the mine atmosphere actuates the time delay mechanism 28. As illustrated in FIG. 8 the high voltage alarm signals from the regulators 16 and 18 are received at terminals 298 and 300 respectively of the time delay mechanism 28. In a similar manner the signal deviation detector 26 supplies a high voltage alarm signal to terminal 302 when the difference between the output signals of the sensor elements 12 and 14 exceeds a preselected value.

The respective alarm signal received at terminals 298, 300, and 302 supplies a base current through diodes 304, 306 and 308 to the transistor 210 after a preselected time interval as determined by resistor 312 and capacitor 314. The collector of transistor 310 is connected to the power source through resistor 316 by terminal 318. A transistor 320 is connected to the collector of transistor 310 by diode 322. Actuating transistor 310 by supplying base current thereto provides base current for transistor 323 to actuate transistor 323. The base current of transistor 320 is terminated to thereby deenergize transistor 320 and switch the collector thereof to a high voltage level. The collector of transistor 320 is connected to the power source at terminal 324 through resistor 326. The emitter of transistor 320 is connected to the electrical ground of the power source at terminal 328. Thus, switching the collector of transistor 320 to a high voltage level generates a latch signal to terminal 330 that is connected to terminal 285 of the alarm device illustrated in FIG. 5 and to terminal 98 of each of the regulators 16 and 18 as illustrated in FIG. 2. In this manner the alarms 280 and 282 are actuated and current through the monitoring circuit 64 of the regulators is terminated to deenergize the sensor assemblies 12 and 14 when an alarm condition continues to exist for a preselected time interval.

In a non-alarm condition transistors 310 and 323 remain in a nonconductive mode. Base current from terminal 318 through resistor 316 and diode 322 maintains transistor 320 in a conductive mode so that current flows from terminal 324 through resistor 326 and transistor 320. Current flow through transistor 320 switches the collector thereof to a low voltage level to prevent generation of a latch signal to terminal 330 and a corresponding deenergization of monitoring circuit 64.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise as specifically illustrated and described.

We claim

1. Electrical circuitry for detecting a combustible mixture of gas in a mine atmosphere comprising,
   sensor means for continuously monitoring the level of combustible gas in the mine atmosphere,
   said sensor means operable to supply output signals proportional to the concentration of the combustible mixture of gas in the mine atmosphere,
   power means for actuating said sensor means,
   regulator means for maintaining a preselected input signal to said sensor means,
   said regulator means having detector means for comparing the output signals of said sensor means with a preselected signal and generating an input signal proportional to said output signals from said sensor means, an alarm device for actuating a preselected alarm signal to indicate the presence of a combustible mixture of gas in the mine atmosphere, said alarm device arranged to receive an output signal from said regulator detector means for actuating the alarm signal when the output signals of said sensor means exceed a preselected value indicating the presence of a combustible mixture of gas in the mine atmosphere, comparator means connected to said regulator means and said power means, said comparator means operable to receive said input signals proportional to said sensor means output signals from said regulator means and to generate a corresponding output signal responsive to the maximum input signal received, meter means connected to said power means and said comparator means for recording the maximum value of the input signals received by said comparator means from said regulator means, and signal deviation detector means for receiving input signals from said regulator means and operable to actuate said alarm device and thereby indicate an excess deviation between the output signals of said sensor means.

2. Electrical circuitry for detecting a combustible mixture of gas in a mine atmosphere as set forth in claim 1 which includes, a time delay mechanism arranged to receive input signals from said regulator detector means and said signal deviation detector means and transmit responsive output signals after a preselected delay interval to said regulator means and said alarm device to terminate said preselected input signal to said sensor means to interrupt operation thereof and actuate said alarm device for continuous operation.

3. Electrical circuitry for detecting a combustible mixture of gas in a mine atmosphere as set forth in claim 1 in which said regulator means includes, a first series regulator connected to said sensor means and operable to maintain a preselected input signal to said sensor means, a first amplifier connected to said sensor means for comparing the input signal applied to said sensor means with a preselected signal, said first amplifier operable to generate an output signal proportional to the signal received from said sensor means, a second series regulator connected to said first amplifier and said first series regulator, and p1 said second series regulator being responsive to the output signal of said first amplifier to supply a corresponding output signal to said first series regulator for adjusting the output signal thereof to maintain a preselected input signal to said sensor means.

4. Electrical circuitry for detecting a combustible mixture of gas in a mine atmosphere as set forth in claim 3 which includes, said first series regulator being operable to maintain a preselected current flow to said sensor means, said first amplifier being operable to compare the current through said sensor means with a preselected signal, and said second series regulator being responsive to the output signal of said first amplifier to supply a corresponding output signal to said first series regulator for adjusting the output signal thereof to maintain a preselected current through said sensor means.

5. Electrical circuitry for detecting a combustible mixture of gas in a mine atmosphere as set forth in claim 3 which includes, said regulator means being operable as a voltage regulator to maintain a preselected voltage across said sensor means, said first amplifier being operable to compare the voltage appearing across said sensor means to a preselected reference voltage, and said first amplifier being further operable to generate in response to a change in the voltage appearing across said sensor means an output signal to said regulator means for maintaining a preselected voltage across said sensor means.

6. Electrical circuitry for detecting a combustible mixture of gas in a mine atmosphere as set forth in claim 3 which includes, means for terminating the input signal from said first series regulator to said sensor means.

7. Electrical circuitry for detecting a combustible mixture of gas in a mine atmosphere as set forth in claim 1 which includes, a silicon controlled rectifier having a gate terminal connected to said alarm device and an anode and a cathode connected across said power means, a resistor for limiting the gate current to said silicon controlled rectifier, and said silicon controlled rectifier operable upon actuation to terminate supply of power to said sensor means upon actuation of said alarm device.

8. Electrical circuitry for detecting a combustible mixture of gas in a mine atmosphere as set forth in claim 1 in which said regulator detector means includes, a detector amplifier for receiving said output signals from said sensor means and transmitting a responsive output signal, feedback means for adjusting the output signal of said detector amplifier to a preselected magnitude proportional to the output signals received from said sensor means, and a comparator amplifier for receiving the output signals of said detector amplifier, said comparator amplifier operable to compare said output signals from said detector amplifier with a preselected voltage applied thereto and to actuate said alarm device when said detector amplifier output signal exceeds said preselected voltage.

9. Electrical circuitry for detecting a combustible mixture of gas in a mine atmosphere as set forth in claim 1 in which said sensor means includes, a pair of sensor assemblies each having a pair of sensor elements connected to said regulator means and arranged to receive a preselected input signal therefrom, and one of said sensor elements having a preselected electrical resistance and being temperature sensitive such that the temperature of said sensor element changes when exposed to a combustible mixture of gas in the mine atmosphere resulting in a change in the electrical resistance of said sensor element.

10. Electrical circuitry for detecting a combustible mixture of gas in a mine atmosphere as set forth in claim 1 in which said comparator means includes, an amplifier for receiving the output signals from said sensor means, and said amplifier connected to said meter means such that the maximum output signal received by said amplifier from said sensor means is recorded by said meter means.

11. Electrical circuitry for detecting a combustible mixture of gas in a mine atmosphere as set forth in claim 10 which includes, said amplifier operable to transmit an output signal responsive to the maximum output signal received from said sensor means, transistor means for receiving the output signal from said amplifier, and said transistor means having an indicator device connected thereto such that output from said transistor means actuates said indicator device to indicate the maximum output signals received from said sensor means.

12. Electrical circuitry for detecting a combustible mixture of gas in a mine atmosphere as set forth in claim 1 in which said signal deviation detector means includes, a first operational amplifier operable to compare a first output signal of said sensor means with a selected percentage of a second output signal of said sensor means, said first operational amplifier operable to switch to a high output state when the first output signal exceeds the selected percentage of the second output signal and thereby supply a corresponding alarm signal for indicating an excess deviation between the first and second signals output signals of said sensor means, a second operational amplifier operable to compare the second output signal of said sensor means with a selected percentage of the first output signal of said sensor means, and said second operational amplifier operable to switch to a high output state when the second output signal exceeds the selected percentage of the first output signal and supply a corresponding alarm signal indicating an excess deviation between the first and second output signals of said sensor means.

13. Electrical circuitry for detecting a combustible mixture of gas in a mine atmosphere as set forth in claim 12 which includes, a trouble circuit for detecting a negative signal generated by said regulator means as indicating a malfunction to said sensor means and said regulator means, said trouble circuit being operable upon detecting a negative signal from said regulator means to actuate said alarm device and generate an alarm signal.

14. Electrical circuitry for detecting a combustible mixture of gas in a mine atmosphere as set forth in claim 1 which includes, a timer for terminating power to said sensor means when said sensor means records an undesirable mixture of combustible gas in the mine after a preselected time delay, said timer operable to continue actuation of said alarm device when an excess mixture of combustible gas is recorded in the mine atmosphere, and said timer connected to said signal deviation detector and said regulator means.

15. Electrical circuitry for detecting a combustible mixture of gas in a mine atmosphere as set forth in claim 1 in which said alarm device includes, a plurality of transistor devices connected to said sensor means and said regulator detector means for receiving output signals therefrom, an audio-visual alarm mechanism arranged to receive output from said transistor devices to indicate the presence of a combustible mixture of gas in the mine, and a silicon controlled rectifier connected to said transistor devices and operable upon actuation to supply an output signal to maintain continuous actuation of said audio-visual alarm mechanism when a combustible mixture of gas exists in the mine atmosphere.

* * * * *